United States Patent
Sachs et al.

(10) Patent No.: US 9,480,441 B2
(45) Date of Patent: Nov. 1, 2016

(54) SYSTEM AND METHOD FOR MEDICAL IMAGING

(71) Applicant: General Electric Company, Schenectady, NY (US)

(72) Inventors: Jonathan Sachs, Tirat Carmel (IL); Yaron Hefetz, Kibbutz Alonim (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/663,763

(22) Filed: Mar. 20, 2015

(65) Prior Publication Data

US 2016/0270744 A1  Sep. 22, 2016

(51) Int. Cl.
*G01T 1/166* (2006.01)
*A61B 6/03* (2006.01)
*A61B 6/04* (2006.01)
*A61B 6/06* (2006.01)
*A61B 6/00* (2006.01)

(52) U.S. Cl.
CPC .............. *A61B 6/037* (2013.01); *A61B 6/0407* (2013.01); *A61B 6/06* (2013.01); *A61B 6/461* (2013.01); *A61B 6/5205* (2013.01); *A61B 6/563* (2013.01)

(58) Field of Classification Search
CPC ...................................................... A61B 6/037
See application file for complete search history.

(56) References Cited

U.S. PATENT DOCUMENTS

2015/0094573 A1\* 4/2015 Bouhnik ............... G01T 1/2985
600/427

OTHER PUBLICATIONS

Georges El Fakhri et al. "Performance of a Novel Collimator for High-Sensitivity Brain Spect"; Med. Phys. 33 (1), Jan. 2006; pp. 209-211.
Jinsong Ouyang et al. "The Design and Manufacture of an Annular Variable-Focusing Collimator for Highsensitivity Brain Spect"; IEEE Transactions on Nuclear Science, vol. 53, No. 5, Oct. 2006.

\* cited by examiner

*Primary Examiner* — David Porta
*Assistant Examiner* — Edwin Gunberg
(74) *Attorney, Agent, or Firm* — Lucas Divine (57) ABSTRACT

A medical imaging system is provided. The imaging system provides patient region-of-interest scanning using a step-staggered detector unit arrangement. A region-of-interest may be a brain. This system can be a Nuclear Medicine (NM) imaging system to acquire Single Photon Emission Computed Tomography (SPECT) image information. The imaging system may comprise CZT detector modules.

20 Claims, 6 Drawing Sheets

SYSTEM AND METHOD FOR MEDICAL IMAGING

BACKGROUND

The subject matter disclosed herein relates generally to medical imaging systems, and more particularly to Nuclear Medicine (NM) imaging systems which can be Single Photon Emission Computed Tomography (SPECT) imaging systems.

In NM imaging, such as SPECT imaging, radiopharmaceuticals are administered internally to a patient. Detectors (e.g., gamma cameras), typically installed on a gantry, capture the radiation emitted by the radiopharmaceuticals and this information is used to form images. The NM images primarily show physiological function of, for example, the patient or a portion of the patient being imaged.

Conventional SPECT imaging systems include one or two gamma cameras mounted to a gantry. In such systems, getting maximum photon count is an issue due to system geometries, distance from an imaging subject, attenuation, and other factors. There is a need for SPECT imaging with improved geometries to capture increased photon counts, which may lead to lower dose and higher image quality.

BRIEF DESCRIPTION

In accordance with an embodiment, an imaging system is provided that includes a gantry, with a bore therethrough; a rotary member attached to the gantry, wherein the rotary member rotates around an axis of the bore; a pair of opposing image detector units attached to the rotary member, wherein each image detector unit is step-staggered; and wherein the system rotates the detector units during an imaging operation. The detector units can output scan data to an image reconstruction module; the image reconstruction module reconstructs the scan data into an image and outputs the image to a display, printer, storage memory, or network. The system can further comprise a second pair of opposing step-staggered detector units attached to the rotary member; and wherein the scanning axis of the first pair of step-staggered detector units is perpendicular to the scanning axis of the second pair of step-staggered detector units in accordance with an embodiment.

The system can further comprise two opposing straight detector units attached to the rotary member; wherein each of the straight detector units comprises one or more gamma cameras arranged in a line; and wherein the scanning axis of the two opposing straight detector units is perpendicular to the scanning axis of the two step-staggered detector units, in accordance with an embodiment. The system can further comprise an image reconstruction module; wherein the step-staggered detector units and straight detector units output scan data to the image reconstruction module; and wherein, for each voxel of the scan data, if the voxel is within an area continuously scanned by all detectors, the image reconstruction module reconstructs the voxel using data from all detectors, and if the voxel is within an area not continuously scanned by all detectors, the image reconstruction module reconstructs the voxel using scan data solely from the step-staggered detectors.

Each image detector unit can comprise a plurality of gamma cameras in the step-staggered arrangement. Further, the plurality of gamma cameras can be adjacently positioned such that substantially no gaps exist between gamma cameras in a detector unit. Each gamma camera can comprise a CZT module and a collimator. In an alternate embodiment, each detector unit detects positron emission tomography (PET) data.

In accordance with an embodiment, an imaging system is provided that includes a gantry, with a bore therethrough; a rotary member attached to the gantry; a plurality of image detectors, each attached to the rotary member by a detector arm, wherein each detector arm can extend and retract an image detector in relation to the rotary member; wherein, in an extended mode, the plurality of image detectors form a pair of opposing step-staggered detector units; and wherein the system rotates the image detectors during an imaging operation. Further, in a step-staggered arrangement, the image detectors are adjacently positioned such that substantially no gaps exist between gamma cameras in a detector unit. Each image detector can comprise a CZT module and a collimator. In accordance with an embodiment, the plurality of image detectors comprises at least six image detectors. The image detectors output scan data to an image reconstruction module; the image reconstruction module reconstructs the scan data into an image; and the system outputs the image to a display, printer, storage memory, or network. In an embodiment, each image detector detects single photon emission computed tomography (SPECT) data. In an alternate embodiment each image detector detects positron emission tomography (PET) data.

The imaging system may further comprise a plurality of additional image detectors, each attached to the rotary member by a detector arm, wherein each detector arm can extend and retract an image detector in relation to the rotary member; wherein, in an extended mode, the plurality of additional image detectors form a pair of opposing straight detector units; and wherein the scanning axis of the two opposing straight detector units is perpendicular to the scanning axis of the two step-staggered detector units. The imaging system may further comprise an image reconstruction module; wherein the step-staggered detector units and straight detector units output scan data to the image reconstruction module; and wherein, for each voxel of the scan data, if the voxel is within an area continuously scanned by all detectors, the image reconstruction module reconstructs the voxel using data from all detectors, and if the voxel is within an area not continuously scanned by all detectors, the image reconstruction module reconstructs the voxel using scan data solely from the step-staggered detectors.

In accordance with an embodiment a non-transitory computer readable storage medium is provided, having stored thereon a computer program comprising instructions, which, when executed by a computer, cause the computer to: receive scan data from an opposing pair of step-staggered detector units and an opposing pair of straight detector units, wherein the two pairs of detector units have rotated around an object during a scan process; reconstruct the scan data into image data, wherein for each voxel of the scan data, if the voxel is within an area continuously scanned by all detectors, the image reconstruction module reconstructs the voxel using data from all detectors, and if the voxel is within an area not continuously scanned by all detectors, the image reconstruction module reconstructs the voxel using scan data solely from the step-staggered detectors; and output the image data to a display, printer, storage memory, or network. Further, each detector unit comprises a plurality of gamma cameras; and the plurality of gamma cameras in each detector unit are adjacently positioned such that substantially no gaps exist between gamma cameras in a detector unit.

DETAILED DESCRIPTION

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of imaging detectors mounted thereto. For example, in various embodiments of an NM imaging system, a Single Photon Emission Computed Tomography (SPECT) imaging scanner is provided that includes a plurality of detectors with detectors that acquire SPECT image information. The various embodiments may include detectors formed from different materials, having different configurations or arrangements, having different collimation, etc. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects inanimate and objects animate.

Figure 1:
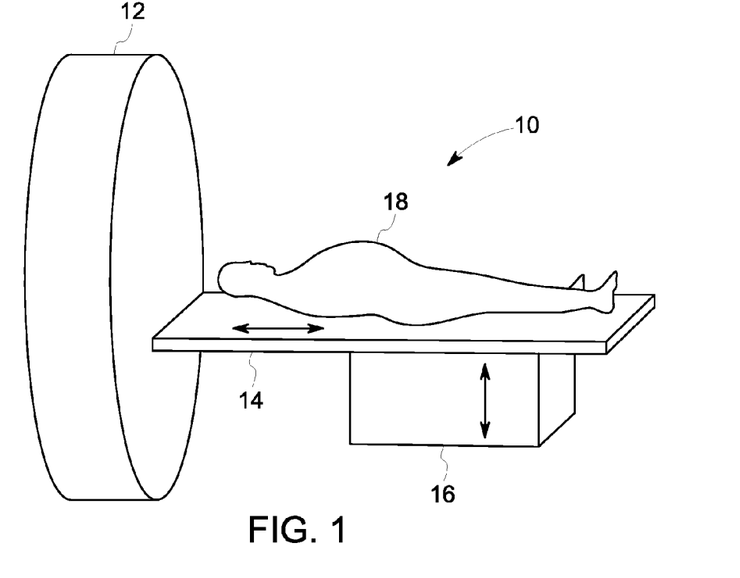
FIG. 1 is a perspective view of a medical imaging system in accordance with an embodiment.

FIG. 1 is a perspective view of a medical imaging system in accordance with an embodiment. A medical imaging system 10 is shown. A subject 18 can be a human patient in an embodiment. Subject 18 can be placed on a pallet 14 that can move a subject horizontally for locating subject 18 in the most advantageous imaging position. The bed mechanism 16 can raise and lower pallet 14 vertically for locating subject 18 in the most advantageous imaging position. Gantry 12 is shown as including an annular bore in an embodiment. In other embodiments, gantry 12 may be an alternate shape, such as square, oval, "C" shape, or hexagonal.

Figure 2:
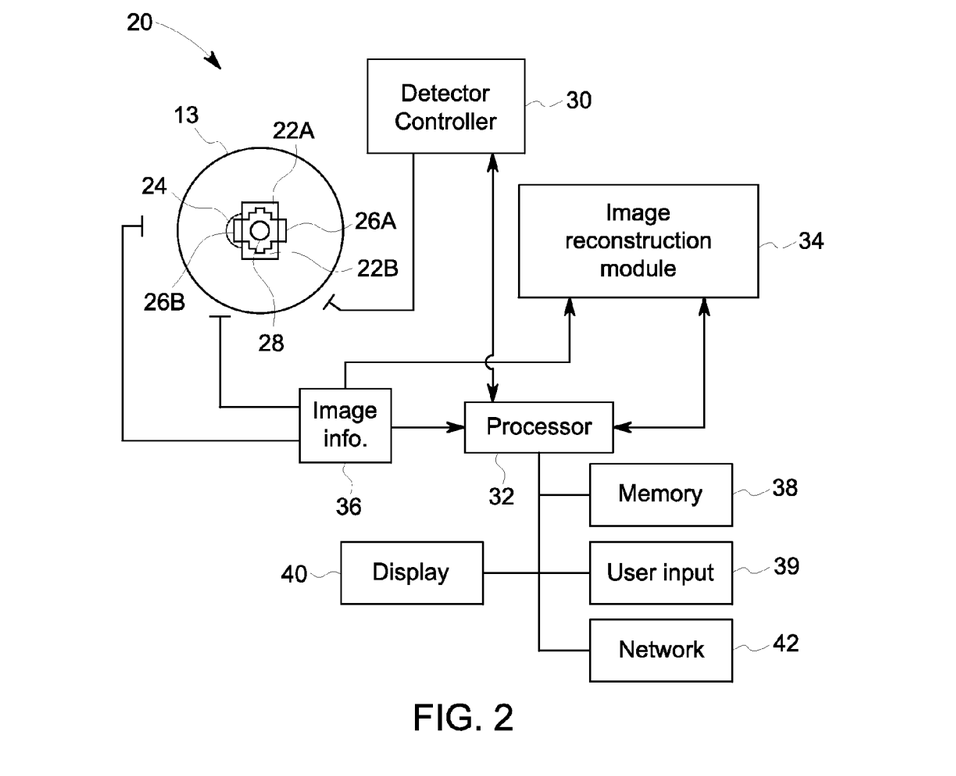
FIG. 2 is a simplified schematic block diagram illustrating a medical imaging system in accordance with an embodiment.

FIG. 2 is a simplified schematic block diagram illustrating a medical imaging system in accordance with an embodiment. A medical imaging system 20 is provided having a plurality of NM cameras configured within detector units. NM cameras may also be referred to as gamma cameras or SPECT cameras. Detector units 22a, 22b, 26a, and 26b may have one or more NM cameras installed therein. Detector units 22a, 22b, 26a, and 26b are attached to a rotary member 13 of gantry 12 in an embodiment. It should be noted that the various embodiments are not limited to the medical imaging system 20 having four detector units as shown or to the sizes or shapes of the illustrated detector units. Medical imaging system 20 in various embodiments is configured as a hybrid SPECT system having a plurality of NM cameras, wherein at least two of the NM cameras are formed from different materials, have different configurations or arrangements, have different collimation, or are otherwise different.

In operation, a subject, such as a patient 24, is positioned such that region of interest (ROI) 28 is positioned near the detector units. Imaging system 20 can then re-adjust the detector units further from or closer to ROI 28, which is a head in an example embodiment. Thus, precision scanning of the brain can be performed. Imaging of ROI 28 is then performed by the detector units. The imaging by each of the gamma cameras within the detector units may be performed simultaneously, concurrently, or sequentially.

Imaging system 20 can adjust before and during the scan. The table mechanism and pallet can adjust the location of the patient. Imaging system 20 can adjust the radial distance of the detector units, as discussed further in relation to FIG. 3, or the detector units may be in a fixed radial distance. Imaging system 20 can rotate detector units around patient 24 and ROI 28. This can be performed by a rotary member 13 installed in the gantry to rotate the detector units around the bore. Detector units may be attached to the rotary member so as to rotate. These adjustments assist in improving the quality and speed of an imaging operation.

Figure 4:
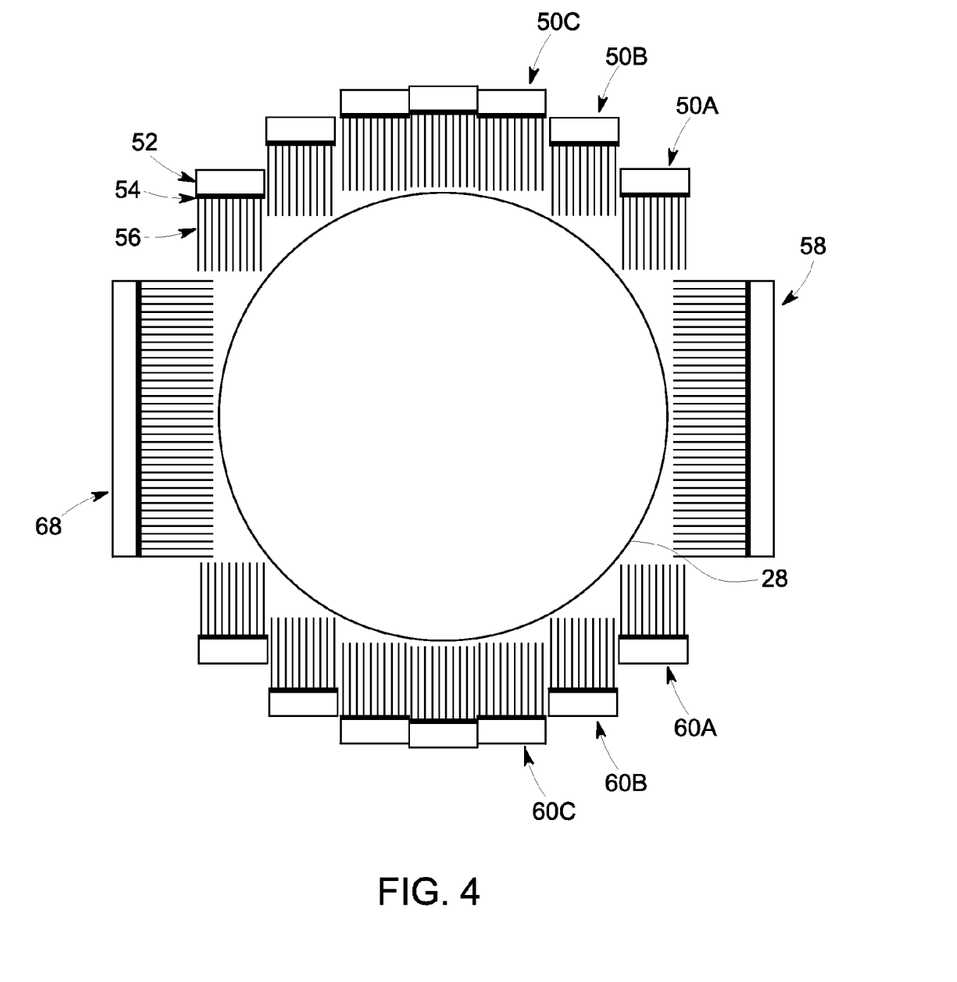
FIG. 4 is a view of an image detector setup in accordance with an embodiment.

Detector unit 22a and detector unit 22b are shown as step-staggered detector units. This allows for the detector unit to be positioned closer to ROI 28. In an embodiment, each of detector unit 22a and detector unit 22b are single units that comprise multiple NM cameras. In an embodiment of FIG. 2, each of detector unit 22a and detector unit 22b include five NM cameras. Step-staggered, for the purposes of this specification, means each successive gamma camera is set further back from an axial center until an apex, after which each successive camera is set further forward towards an axial center. This is shown in FIG. 2 and FIG. 4, as examples. Detector unit 22a and detector unit 22b are shown as facing each other and substantially symmetrical to each other across ROI 28. Put another way, the detector units are opposingly symmetrical across ROI 28.

Detector unit 26a and detector unit 26b are shown as straight detector units. In an embodiment, each of detector unit 26a and detector unit 26b are single units that comprise one or more NM cameras. In an embodiment of FIG. 2, each of detector unit 26a and detector unit 26b include four NM cameras. Detector unit 26a and detector unit 26b are aligned such that the top and bottom edges line up with the side edges of detector unit 22a and detector unit 22b as shown in FIG. 2. No gaps in collimator coverage exist in the embodiment of FIG. 4, as an example. This provides increased coverage of photon emission angles from ROI 28. Detector unit 26a and detector unit 26b are shown as opposing and substantially symmetrical to each other across ROI 28. FIG. 2 shows the pair of step-staggered detector units (22a and 22b) having a perpendicular scanning axis to that of the straight detector units (26a and 26b). The combinations of detector units 22a, 22b, 26a, and 26b can be expressed as a fixed ring detector.

Imaging system 20 further comprises a detector controller 30 that operates to control the movement of the detector units. For example, the detector controller 30 may control movement of the detector units, such as to rotate or orbit the detector units around ROI 28. Detector controller 30 may control the orbital rotation of the detector units around the edges of the gantry bore, such that the detector units are at a new angle to ROI 28 than previously.

Imaging system 20 further comprises an image reconstruction module 34 configured to generate images from acquired image information 36 received from the detector units 22a, 22b, 26a, and 26b. For example, image reconstruction module 34 may operate using NM image reconstruction techniques to generate SPECT images of patient 24, which may include ROI 28. Image reconstruction module 34 may be implemented in connection with or on detector controller 30 and/or processor 32 that is coupled to imaging system 20. Optionally, image reconstruction module 34 may be implemented as a module or device that is coupled to or installed in the detector controller 30 and/or processor 32. Each processing module may be a separate hardware module or software module, or combined together into one chip or module in various embodiments.

Image information 36 received by the processor 32 and/or image reconstruction module 34 may be stored for a short term (e.g., during processing) or for a long term (e.g., for later offline retrieval) in a memory 38. Memory 38 may be any type of data storage device, which may also store databases of information. Memory 38 may be separate from or form part of the processor 32. A user input 39, which may include a user interface selection device, such as a computer mouse, touchscreen, trackball, keyboard and/or user input types is also provided to receive a user input. User input 39 may direct processor 32 to send a detector control signal to detector controller 30 for alteration of the detector unit arrangement in the gantry bore. Optionally, user input 39 may be considered by the processor 32 as a suggestion and the processor 32 may choose to not execute the suggestion based on criteria.

Thus, during operation, the output from the detector units, which may include image information 36, such as scan data from a plurality of detector/gantry angles, is transmitted to processor 32 and image reconstruction module 34 for reconstruction and formation of one or more images. Images may be output as two-dimensional (2D), three-dimensional (3D), and/or four-dimensional (4D). The reconstructed images and other user output can be transmitted to a display 40 such as a computer monitor or printer output. The reconstructed images and other user output can also be transmitted to a remote computing device via network 42.

Figure 3:
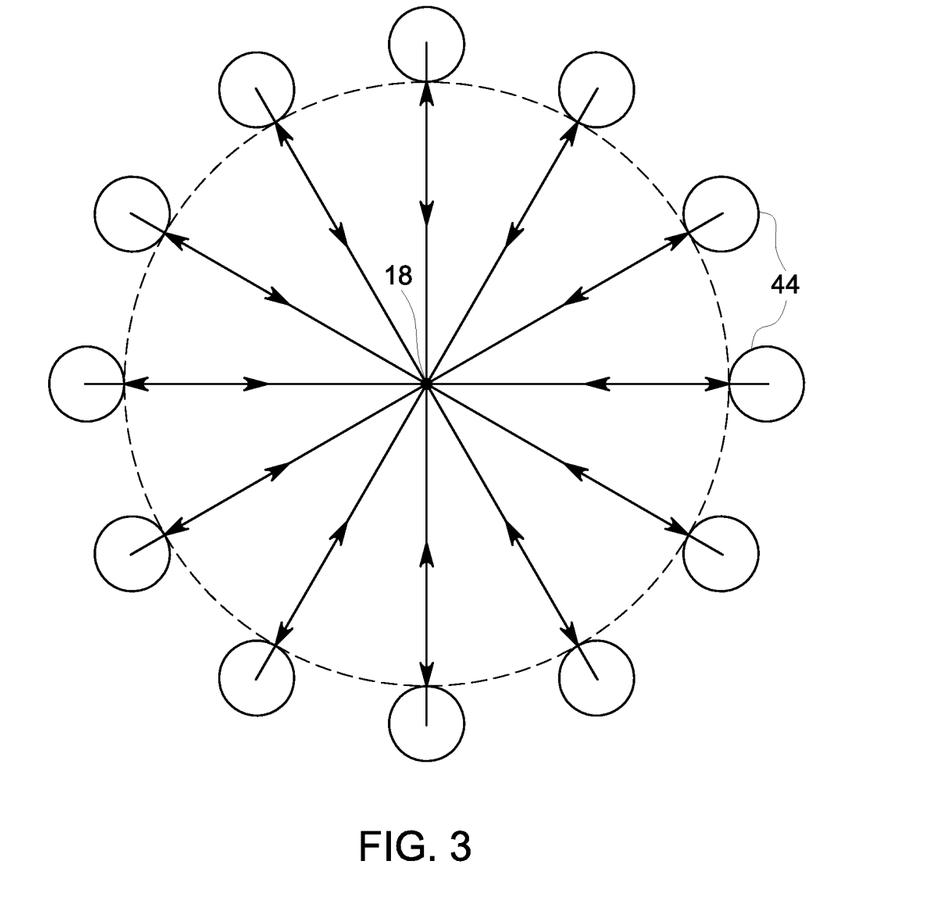
FIG. 3 is a diagram illustrating a radial construction and approach to image detection in accordance with an embodiment.

FIG. 3 is a diagram illustrating a radial construction and approach to image detection in accordance with an embodiment. FIG. 3 shows a radial construction of an imaging system where twelve image detectors 44 are placed at a consistent angle, thirty degrees in this example, from each other along the inside of a gantry bore. Thus, image detectors 44 are uniformly distributed in this example. Each image detector 44 is movable along a radial axis by an arm that may include motors. Such an arm may extend and retract the detector unit. Such an arm may attach to gantry 12 or rotary member 13. This allows image detectors 44 to be closer or further from a subject 18 for imaging. Image detectors 44 are shown along the dotted line as their outer limit position in this view of one embodiment. The dual head radial arrows depict the in-out direction of motion of image detectors 44. FIG. 3 shows an embodiment where image detectors can extend and retract for positioning to a patient. In an alternate embodiment, the detector unit setup, such as shown in FIG. 2, may be fixed in an axial direction. In both the embodiment of FIG. 2 and the embodiment of FIG. 3, detector units and image detectors rotate orbitally around a subject.

While FIG. 3 shows the detector arms attached at a consistent angle from one another, the arms may be attached at any angle around the circumference of the bore.

FIG. 4 is a view of an image detector setup in accordance with an embodiment. FIG. 4 shows an embodiment where ROI 28 may be a brain. FIG. 4 shows detector unit 50a, 50b, 50c, 58, 60a, 60b, 60c, and 68. Each detector unit comprises one or more NM cameras, each comprising an image detection module 52, or application specific integrated circuit (ASIC), an image detection material 54, and a collimator 56. Image detection material 54 can be a CZT crystal in an embodiment, as discussed further below.

Detector units 50a, 50b, and 50c are positioned in a step-staggered arrangement. This can be in the fixed ring setup of FIG. 2 or having been positioned by extendable arms of FIG. 3. Detector units 60a, 60b, and 60c are positioned in a step-staggered arrangement, and are shown as substantially symmetrical to detector units 50a, 50b, and 50c across ROI 28. In FIG. 4, the step-staggered arrangement covers the field of view of ROI 28. In FIGS. 4, 50a, 50b, 50c, 60a, 60b, and 60c are all sown of similar width. In an alternate embodiment, 50a and 60a, as examples, could be of a smaller width so as line up with the edge of the field of view. This could save cost by not needing as large of detector in some instances.

Detector unit 58 and detector unit 68 are shown as straight detector units. In an alternate embodiment, four NM cameras the size of detector unit 50a may be positioned adjacent to one another to create the same coverage of a single detector unit 58 or detector unit 68. In an embodiment, detector unit 58 and detector unit 68 are positioned so that their collimators do not block any photons that would travel towards any of the step-staggered detector units. Detector unit 58 is shown as substantially symmetrical to detector unit 68 across ROI 28. In an alternate embodiment, the system of FIG. 4 can operate without detector units 58 and 68. In an alternate embodiment, the system of FIG. 4 could have step-staggered detector unit arrangements on all four sides.

The embodiments of FIG. 4 and throughout optimize the surface of image detection by providing substantially continuous coverage between the step-staggered detector units.

In addition, the step-staggered configuration allows the detector units to be closer to ROI 28 to provide improved image detection. Both the step-staggered configuration and the close positioning improve photon counts, which can improve image output and reduce the amount of dose needed to acquire sufficient images.

Detector units may be thought of as one or more NM cameras, depending on specific implementation. Thus, for example the detector unit 50*a* may be a single NM camera implementation, and detector unit 58 may comprise four NM cameras in implementation. FIG. 4 shows seven NM cameras in each step-staggered arrangement and four in each straight arrangement. Thus, the system shown in FIG. 4 can include twenty-two total NM cameras in an embodiment.

In a fixed configuration where multiple NM cameras are in one detector unit, such as in FIG. 2, the NM cameras are placed adjacent to each other with no gaps in coverage in the direction of the collimators. In a configuration with detector units that have individual radial extension and retraction, such as in FIG. 3 and FIG. 4, the detector units with gamma cameras are placed adjacent to each other with substantially no gaps in coverage in the direction of the collimators. Substantially no gaps entails that the detector units are as close as possible without causing friction by the contact of the side surfaces of the detector units. This may be solved with a miniscule air gap or a miniscule lubricant gap, wherein the lubricant is one that is placed specifically to reduce movement friction between the detector units. Miniscule, in some embodiments, can mean less than 1 millimeter. In some systems, side shielding is placed on a NM camera or detector unit to prevent photons from the side angle. In the embodiment of FIG. 4, no side shielding is needed as the collimator from a neighboring NM camera will block the side. Thus, there are no gaps in coverage that would be created from side shielding in an embodiment. If side shielding were added in an alternate embodiment, it would be of miniscule (less than one millimeter) width so as the system still operates with substantially no gaps between detectors.

Collimator 56 is shown as a parallel hole collimator. Collimator 56 may have thick septa or thin septa depending on the specific application. Collimator 56 may of different configurations, such as pin-hole, fan-beam, converging, diverging, cone-beam, or others known in the art for NM applications.

NM cameras are implemented as CZT modules in an embodiment. CZT modules are rectangular modules in an embodiment. CZT modules are based on a crystal of Cadmium Zinc Telluride (CdZnTe). In alternate embodiments, NM cameras may include single crystal, or multi-crystal, detectors or pixelated detectors or scintillator based detectors that are configured to acquire SPECT image data. For example, NM cameras may be formed from different materials, such as semiconductor materials, including CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum(III) bromide (LaBr$_3$), among others. Additionally suitable components may be provided. For example, the detector units may be coupled to photosensors, such as an array of Photo-Multiplier Tubes (PMTs), an Avalanche Photodiode Detector (AFD), etc.

The configuration of FIG. 4 increases the NM camera count, reduces gaps in detection coverage (increasing surface of detection), and reduces distance to the ROI. Thus, more photons can be detected in an imaging operation. The configuration of FIG. 4 is an improved geometry for rectangular CZT modules.

In an alternate embodiment, the ring of FIG. 4 noted as ROI 28 could be a tube cover or scan window to provide protection and safety to a patient. Thus, the region of interest and the patient portions would be within the ring. One or more extra layers of protection can be implemented. This is helpful as the detector units rotate orbitally around the patient.

Figure 5:
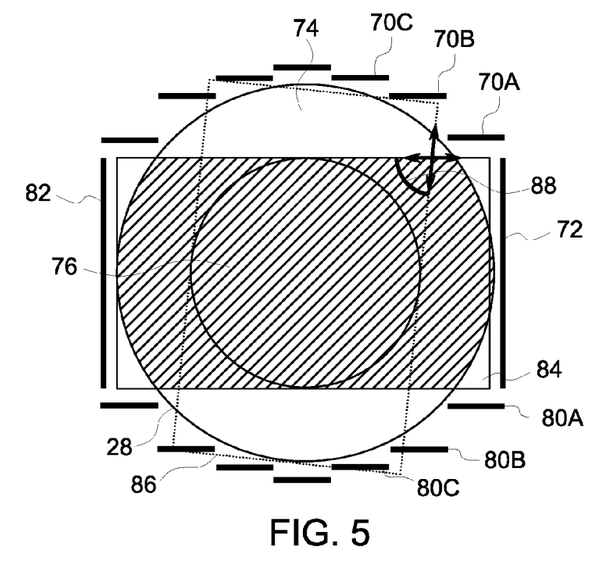
FIG. 5 is a scanning view of a medical imaging system in accordance with an embodiment.

FIG. 5 is a scanning view of a medical imaging system in accordance with an embodiment. FIG. 5 shows detector unit edges 70*a*, 70*b*, 70*c*, 80*a*, 80*b*, 80*c*, 72, and 82. These illustrate the ends of collimators of FIG. 4. FIG. 5 shows a fixed ring detector unit system during a scanning operation. The system orbits, or rotates around, the region of interest during an operation. The system generally orbits a minimum of 180 degrees. Scanning window 84 shows the angular sampling of photons created by pair of detector unit 72 and detector unit 82 at the initial position of the fixed ring detector unit system. Scanning window 86 shows the angular sampling of photons created by pair of detector unit 72 and detector unit 82 at a subsequent orbital position during a scanning operation. Scanning window 84 is offset by angle 88 from scanning window 86.

Full scan zone 76 is an area of the region of interest that is always within the scanning windows of detector unit 72 and detector unit 82. This is preferential in the system, because this center region may have the most distance for the photons to travel. This distance increases the amount of attenuation potentially caused by water, tissue, and other matter in a subject. Thus, in this embodiment, full scan zone 76 is always being scanned by the step-staggered detector units (e.g. 70*a*, 70*b*, 70*c*, 80*a*, 80*b*, 80*c*) and straight line detector units (e.g. 72 and 82) to increase the amount of photon detection, sensitivity, in this area. Partial scan zone 78, shown as an outer ring, or area, in this embodiment, is not continuously sampled by straight line detector units 72 and 82. Further, if rotation is continuous, two temporally discrete transaxial images can be reconstructed per rotation.

Figure 6:
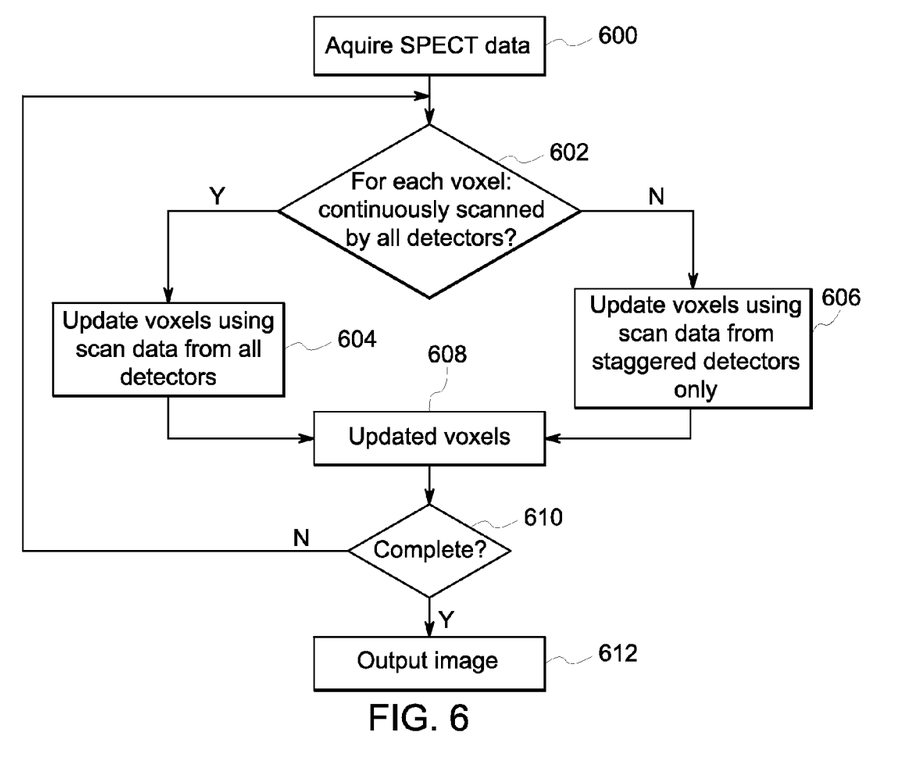
FIG. 6 is an image reconstruction method in accordance with an embodiment.

FIG. 6 is an image reconstruction method in accordance with an embodiment. FIG. 6 shows exemplary steps that image reconstruction module 34 and/or processor 32 may execute in order to reconstruct image information 36 to an image to be output to a display 40, printer, and/or network 42. FIG. 6 shows a reconstruction algorithm to take into account the full scan zone and partial scan zone of FIG. 5. This algorithm and method steps can be implemented in computer program code stored on a computer readable medium, such as memory 38. Other image reconstruction steps may occur in the system, FIG. 6 illustrates additional specific steps for improved image reconstruction based on the physical scanning embodiments disclosed herein.

In step 600 the system performs a NM imaging scan, collecting photon count information from a radiopharmaceutical inside a subject, for example. In operation, the detector units are rotated around the subject region of interest to acquire count information. This creates SPECT scan data as image information 36. This scan could alternately be a PET imaging scan. Next, image reconstruction begins.

In step 602, the system determines whether a particular voxel was included in full scan zone 76, i.e. that it was continuously scanned by all detectors. If the voxel was in full scan zone 76, the system proceeds to step 604. If the voxel was not in full scan zone 76, but instead in partial scan zone 74, the system proceeds to step 606.

In step 604, the system updates (i.e. reconstructs) the voxel using scan data from all detector units. This includes both side-staggered detector units and straight line detector units.

In step 606, the system updates (i.e. reconstructs) the voxel using scan data from side-staggered detector units only. These areas may still have a high photon count as they are closer to the edge of the scanned object, and thus likely have less attenuation. This can save reconstruction time because less scan data is needed for reconstruction.

In step 608, the system provides the updated voxels and proceeds to step 610. In step 610, the system returns to evaluate the next voxel if the image reconstruction is incomplete. As the reconstruction is iterative, the system performs iterations until image reconstruction is complete. When complete, the system can output a reconstructed image in step 612.

Figure 7:
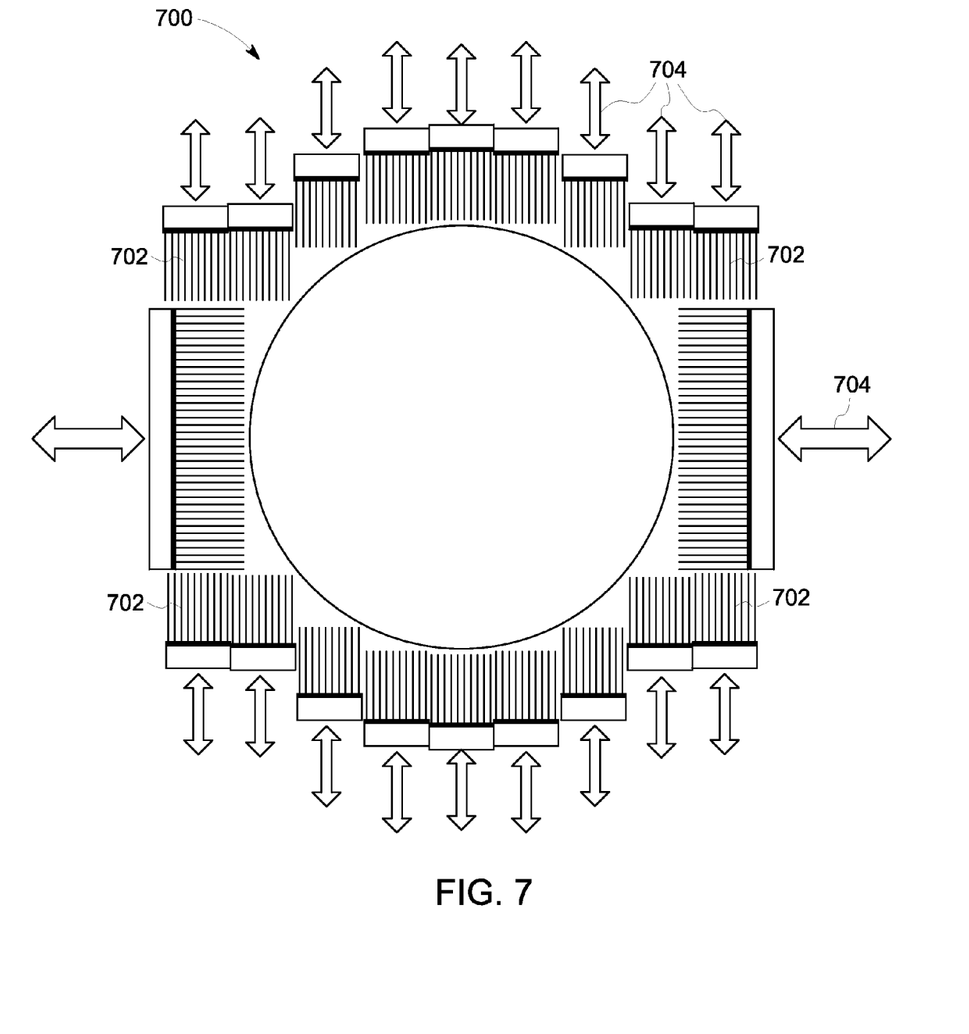
FIG. 7 is a view of an extended image detector system in accordance with an embodiment.

FIG. 7 is a view of an extended image detector system 700 in accordance with an embodiment. The detector units are shown as extended in further towards a smaller region of interest. Inactive detector units 702 are set as inactive for the current imaging scan. Inactive detector units 702 thus do not waste energy by being on when not needed. Direction arrows 704 show the direction of extension and retraction of detector unit arms (not shown in FIG. 7) for positioning of the detector units. For a smaller region of interest, such as a head comprising a brain, the system can extend further to get closer to the region of interest. This provides improved image scanning.

Figure 8:
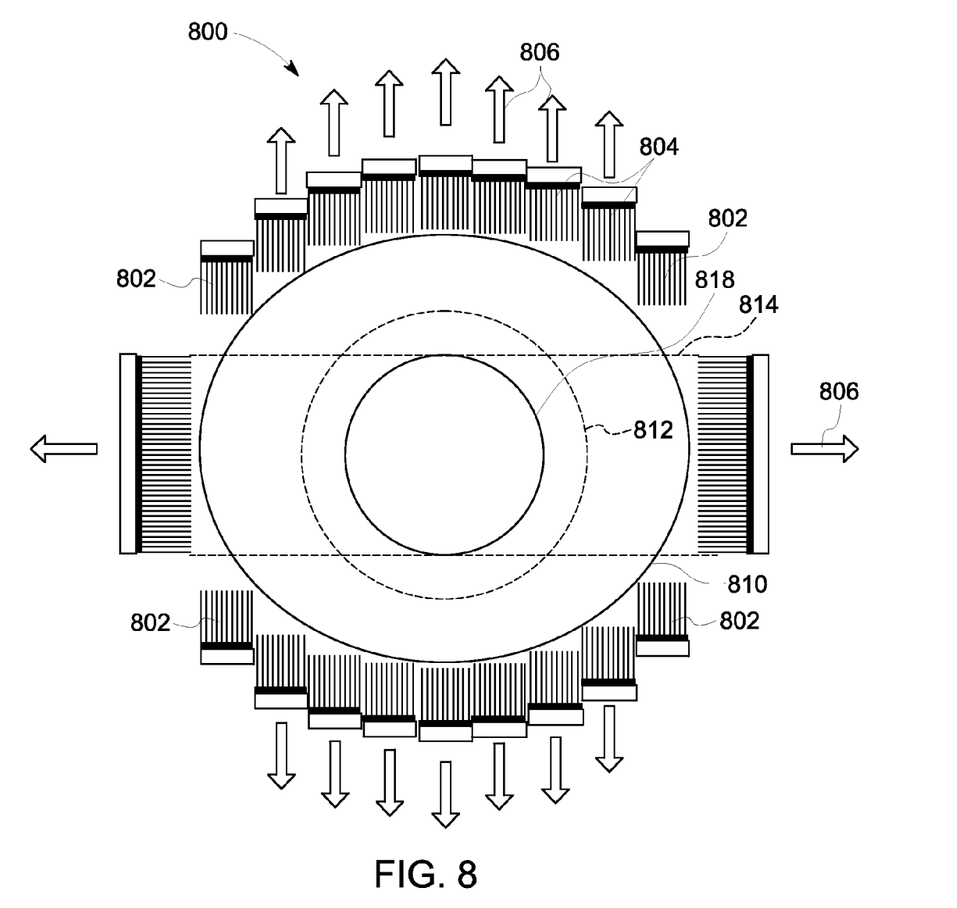
FIG. 8 is a view of a retracted image detector system in accordance with an embodiment.

FIG. 8 is a view of a retracted image detector system 800 in accordance with an embodiment. A larger region of interest 810 is being imaged than the smaller region of interest 812 of FIG. 7. Retracted detector units 804 are active for scanning. Arrows 806 show the direction of retraction by arms (not shown in FIG. 8) attached to the detector units and a rotary member attached to the stationary gantry. Active detector units 802 have not moved. These active detector units 802 have now been activated for usage because the region of interest is larger in the image scanning operation of FIG. 8. Thus, active detector units 802 correspond to inactive detector units 702. All detector units can be activated and deactivated for particular scans, inactive detector units 702 corresponding to active detector units 802 are explained as an example. For the larger region of interest 810, the scanning window 814 provides less coverage, and so the proportion of larger region of interest 810 that is included in full scan zone 818 is less than the proportion of a smaller region of interest, shown in FIG. 5, for example.

As contemplated, the various embodiments provide a higher resolution, quicker imaging system that may not need as much patient dose to achieve high quality images. The system is reconfigurable to scan regions of interest of varying sizes.

The configurable and controllable system of some embodiments could be controlled by user input. Thus, the user can override the automatic operation of the system and take full specific control of components of the system through a user interface.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
   a gantry, with a bore therethrough;
   a rotary member attached to the gantry, wherein the rotary member rotates around an axis of the bore;
   a first pair of opposing first image detector units attached to the rotary member, wherein each first image detector unit comprises a plurality of gamma cameras in a step-staggered arrangement;
   a second pair opposing straight detector units attached to the rotary member, wherein each of the straight detector units comprises one or more gamma cameras arranged in a line; and
   wherein the scanning axis of the two opposing straight detector units is perpendicular to the scanning axis of the two step-staggered detector units; and
   wherein the system rotates the detector units around the circumference of the bore during an imaging operation.

2. The imaging system of claim 1, wherein
   the plurality of gamma cameras in the first image detector units are adjacently positioned such that gaps between gamma cameras in a detector unit are less than 1 millimeter.

3. The imaging system of claim 2, wherein
   at least one gap is lubricated.

4. The imaging system of claim 1, wherein
   each gamma camera comprises a CZT module and a collimator.

5. The imaging system of claim 1, further comprising
   an image reconstruction module;
   wherein the step-staggered first detector units and straight detector units output scan data to the image reconstruction module; and
   wherein, for each voxel of the scan data, if the voxel is within an area continuously scanned by all detector units, the image reconstruction module reconstructs the voxel using data from all detector units, and if the voxel is within an area not continuously scanned by all detector units, the image reconstruction module reconstructs the voxel using scan data solely from the step-staggered first detector units.

6. The imaging system of claim 1, wherein
   the detector units output scan data to an image reconstruction module;
   the image reconstruction module reconstructs the scan data into an image and outputs the image to a display, printer, storage memory, or network.

7. The imaging system of claim 1, wherein
   each detector unit detects positron emission tomography (PET) data.

8. The imaging system of claim 1, wherein
   each gamma camera comprises an image detection module, an image detection material, and a collimator.

9. The imaging system of claim 1, wherein
   at least one gamma camera is set as inactive for an imaging scan.

10. An imaging system, comprising:
    a gantry, with a bore therethrough;
    a rotary member attached to the gantry;
    a plurality of first image detectors, each attached to the rotary member by a detector arm, wherein each detector arm can extend and retract a first image detector in relation to the rotary member;
    wherein, in an extended mode, the plurality of first image detectors form a pair of opposing step-staggered detector units;
    a plurality of second image detectors, each attached to the rotary member by a detector arm, wherein each detector arm can extend and retract a second image detector in relation to the rotary member;
    wherein, in an extended mode, the plurality of additional image detectors form a pair of opposing straight detector units; and
    wherein the scanning axis of the plurality of first detector units is perpendicular to the scanning axis of the plurality of second detector units; and
    wherein the system rotates the image detectors during an imaging operation.

11. The imaging system of claim 10, wherein
    each image detector comprises a CZT module and a collimator.

12. The imaging system of claim 10, wherein
    the plurality of first image detectors comprises at least six image detectors.

13. The imaging system of claim 10, further comprising
    an image reconstruction module;
    wherein the step-staggered plurality of first detector units and straight plurality of second detector units output scan data to the image reconstruction module; and
    wherein, for each voxel of the scan data, if the voxel is within an area continuously scanned by all detectors, the image reconstruction module reconstructs the voxel using data from all detectors, and if the voxel is within an area not continuously scanned by all detectors, the image reconstruction module reconstructs the voxel using scan data solely from the step-staggered plurality of first detectors.

14. The imaging system of claim 10, wherein
    the image detectors output scan data to an image reconstruction module;
    the image reconstruction module reconstructs the scan data into an image; and
    the system outputs the image to a display, printer, storage memory, or network.

15. The imaging system of claim 10, wherein
    each image detector detects single photon emission computed tomography (SPECT) data.

16. The imaging system of claim 10, wherein
    each image detector detects positron emission tomography (PET) data.

17. The imaging system of claim 10, wherein
at least one image detector is set as inactive for an imaging scan.

18. The imaging system of claim 10, wherein
each image detector comprises an image detection module, an image detection material, and a collimator.

19. A non-transitory computer readable storage medium having stored thereon a computer program comprising instructions, which, when executed by a computer, cause the computer to:
receive scan data from an opposing pair of step-staggered detector units and an opposing pair of straight detector units, wherein the two pairs of detector units have rotated around an object during a scan process;
reconstruct the scan data into image data, wherein for each voxel of the scan data, if the voxel is within an area continuously scanned by all detector units, the computer reconstructs the voxel using data from all detector units, and if the voxel is within an area not continuously scanned by all detector units, the computer reconstructs the voxel using scan data solely from the step-staggered detector units; and
output the image data to a display, printer, storage memory, or network.

20. The non-transitory computer readable storage medium of claim 19, wherein
each detector unit comprises a plurality of gamma cameras; and
the plurality of gamma cameras in each detector unit are adjacently positioned such that gaps between gamma cameras in a detector unit are less than 1 millimeter.

* * * * *